US012788881B2

(12) United States Patent
Kurzman et al.

(10) Patent No.: US 12,788,881 B2
(45) Date of Patent: Nov. 10, 2026

(54) FLUID DELIVERY PUMP VALVE ASSEMBLY

(71) Applicant: Insulet Corporation, Acton, MA (US)

(72) Inventors: Maya Kurzman, Marlboro, NJ (US); Steven Cardinali, Tewksbury, MA (US); Kyle Breingan, Lowell, MA (US)

(73) Assignee: INSULET CORPORATION, Acton, MA (US)

( * ) Notice: Subject to any disclaimer, the term of this patent is extended or adjusted under 35 U.S.C. 154(b) by 1035 days.

(21) Appl. No.: 17/715,536

(22) Filed: Apr. 7, 2022

(65) Prior Publication Data

US 2022/0323674 A1 Oct. 13, 2022

Related U.S. Application Data

(60) Provisional application No. 63/171,813, filed on Apr. 7, 2021.

(51) Int. Cl.
*A61M 5/168* (2006.01)
*A61M 5/142* (2006.01)

(52) U.S. Cl.
CPC .... *A61M 5/16881* (2013.01); *A61M 5/14244* (2013.01); *A61M 5/16813* (2013.01); *A61M 2205/0266* (2013.01)

(58) Field of Classification Search
CPC ........... F16K 2099/0069; F16K 31/502; F04B 7/0061; A61M 39/22; A61M 2039/226;
(Continued)

(56) References Cited

U.S. PATENT DOCUMENTS 1,441,508 A 1/1923 Jensen
2,897,214 A 7/1959 Chamberlin et al.
(Continued)

FOREIGN PATENT DOCUMENTS

EP 3047873 A1 * 7/2016 .......... A61M 25/003
EP 3135965 A1 3/2017
(Continued)

OTHER PUBLICATIONS

International Preliminary Report on Patentability for the International Patent Application No. PCT/US2019/042160, mailed Jan. 28, 2021, 12 pages.
(Continued)

*Primary Examiner* — Courtney Fredrickson
*Assistant Examiner* — Kayla M. Turkowski
(74) *Attorney, Agent, or Firm* — Goodwin Procter LLP

(57) ABSTRACT

Wearable fluid delivery devices and pump systems having a bistable valve for setting a fluid path in one of a fluid fill state or a fluid delivery state are described. For example, in one embodiment, a fluid pump system for a wearable fluid delivery device may include a pump chamber to store a fluid, a fluid path valve operable with the pump chamber, the fluid path valve may include a fixed portion and a movable portion, a shaft configured to move along the fixed portion to engage the movable portion responsive to a force imparted by an actuator, the movable portion comprising an offset to deflect movement of the shaft to cause the movable portion to pivot from one of a first position to a second position to the other of the first position or the second position responsive to being engaged by the shaft. Other embodiments are described.

19 Claims, 14 Drawing Sheets

(58) Field of Classification Search
CPC .......... A61M 5/16881; A61M 5/16813; A61M 2205/0266
See application file for complete search history.

(56) References Cited

U.S. PATENT DOCUMENTS

| | | | |
|---|---|---|---|
| 3,579,805 A | 5/1971 | Kast | |
| 4,537,387 A * | 8/1985 | Danby | A61M 5/16881 604/249 |
| 4,833,088 A | 5/1989 | Desimone et al. | |
| 5,232,668 A | 8/1993 | Grant et al. | |
| 5,244,459 A | 9/1993 | Hill | |
| 5,622,413 A * | 4/1997 | Kim | B60T 8/17616 303/119.2 |
| 5,995,236 A | 11/1999 | Roth et al. | |
| 6,142,181 A | 11/2000 | Schumacher | |
| 6,200,293 B1 | 3/2001 | Kriesel et al. | |
| 6,418,332 B1 | 7/2002 | Mastrototaro et al. | |
| 6,514,460 B1 | 2/2003 | Fendrock | |
| 6,740,059 B2 | 5/2004 | Flaherty | |
| 6,768,425 B2 | 7/2004 | Flaherty et al. | |
| 7,137,964 B2 | 11/2006 | Flaherty | |
| 7,303,549 B2 | 12/2007 | Flaherty et al. | |
| 7,731,900 B2 | 6/2010 | Haar et al. | |
| 7,842,241 B2 | 11/2010 | Arbogast et al. | |
| 7,846,385 B2 | 12/2010 | Arbogast et al. | |
| 7,846,386 B2 | 12/2010 | Arbogast et al. | |
| 7,846,387 B2 | 12/2010 | Arbogast et al. | |
| 7,846,388 B2 | 12/2010 | Arbogast et al. | |
| 7,867,446 B2 | 1/2011 | Arbogast et al. | |
| 7,897,107 B2 | 3/2011 | Arbogast et al. | |
| 7,914,742 B2 | 3/2011 | Arbogast et al. | |
| 8,003,052 B2 | 8/2011 | Sacherer | |
| 8,080,205 B2 | 12/2011 | Arbogast et al. | |
| 8,431,408 B2 | 4/2013 | Lewis et al. | |
| 8,465,977 B2 | 6/2013 | Joseph et al. | |
| 8,701,264 B2 | 4/2014 | Martinson | |
| 8,765,482 B2 | 7/2014 | Joseph et al. | |
| 8,894,262 B2 | 11/2014 | Celentano et al. | |
| 9,265,877 B2 | 2/2016 | Mcarthur | |
| 9,572,926 B2 | 2/2017 | Cabiri | |
| 9,814,832 B2 | 11/2017 | Agard et al. | |
| RE47,100 E | 10/2018 | Smith et al. | |
| 10,661,012 B2 | 5/2020 | Nazzaro et al. | |
| 2004/0116847 A1 | 6/2004 | Wall | |
| 2005/0009126 A1 | 1/2005 | Andrews et al. | |
| 2005/0125162 A1 | 6/2005 | Hajizadeh et al. | |
| 2005/0201897 A1 | 9/2005 | Zimmer et al. | |
| 2005/0232815 A1 | 10/2005 | Ruhl et al. | |
| 2005/0238507 A1 | 10/2005 | Dilanni et al. | |
| 2005/0277164 A1 | 12/2005 | Drucker et al. | |
| 2009/0204078 A1 | 8/2009 | Mitchell et al. | |
| 2009/0254041 A1 | 10/2009 | Krag et al. | |
| 2009/0282947 A1 | 11/2009 | Powell | |
| 2010/0152658 A1 | 6/2010 | Hanson et al. | |
| 2010/0168683 A1 | 7/2010 | Cabiri | |
| 2010/0317951 A1 | 12/2010 | Rutkowski et al. | |
| 2011/0071765 A1 | 3/2011 | Yodfat et al. | |
| 2011/0193704 A1 | 8/2011 | Harper et al. | |
| 2011/0218495 A1 | 9/2011 | Remde | |
| 2011/0289497 A1 | 11/2011 | Kiaie et al. | |
| 2012/0095316 A1 | 4/2012 | Lewis et al. | |
| 2012/0201048 A1 | 8/2012 | Prais | |
| 2013/0204130 A1 | 8/2013 | Mcarthur et al. | |
| 2014/0012119 A1 | 1/2014 | Geaghan et al. | |
| 2014/0054883 A1 | 2/2014 | Lanigan et al. | |
| 2014/0074033 A1 | 3/2014 | Sonderegger et al. | |
| 2014/0078263 A1 | 3/2014 | Kim | |
| 2014/0131199 A1 | 5/2014 | Simmons et al. | |
| 2014/0148784 A1 | 5/2014 | Anderson et al. | |
| 2014/0254170 A1 | 9/2014 | Celentano et al. | |
| 2014/0296787 A1 | 10/2014 | Agard et al. | |
| 2014/0316379 A1 | 10/2014 | Sonderegger et al. | |
| 2015/0283335 A1 | 10/2015 | Lin | |
| 2015/0338349 A1 | 11/2015 | Carter et al. | |
| 2015/0361154 A1 | 12/2015 | Jowett et al. | |
| 2015/0366945 A1 | 12/2015 | Greene | |
| 2016/0015891 A1 | 1/2016 | Papiorek | |
| 2016/0038689 A1 | 2/2016 | Lee et al. | |
| 2016/0058941 A1 | 3/2016 | Wu et al. | |
| 2016/0135747 A1 | 5/2016 | Frey et al. | |
| 2016/0310665 A1 | 10/2016 | Hwang et al. | |
| 2017/0028132 A1 | 2/2017 | Cronenberg et al. | |
| 2017/0106138 A1 | 4/2017 | Cabiri | |
| 2017/0189270 A1 | 7/2017 | Nazzaro et al. | |
| 2017/0214584 A1 | 7/2017 | Kanojia et al. | |
| 2017/0234858 A1 | 8/2017 | Depa et al. | |
| 2017/0348479 A1 | 12/2017 | Choate et al. | |
| 2017/0354785 A1 | 12/2017 | Gazeley et al. | |
| 2018/0015274 A1 | 1/2018 | Haury et al. | |
| 2018/0075200 A1 | 3/2018 | Davis et al. | |
| 2018/0207357 A1 | 7/2018 | John | |
| 2018/0236173 A1 | 8/2018 | Mccaffrey et al. | |
| 2018/0256815 A1 | 9/2018 | Nazzaro | |
| 2018/0307515 A1 | 10/2018 | Meller et al. | |
| 2019/0022317 A1 | 1/2019 | Uddin et al. | |
| 2019/0091404 A1 | 3/2019 | Nazzaro et al. | |
| 2019/0132801 A1 | 5/2019 | Kamath et al. | |
| 2019/0167895 A1 | 6/2019 | Dechellette et al. | |
| 2019/0240417 A1 | 8/2019 | Hostettler et al. | |
| 2019/0321545 A1 | 10/2019 | Saint | |
| 2020/0197605 A1 | 6/2020 | Haidar | |
| 2020/0261643 A1 | 8/2020 | Boyaval et al. | |
| 2020/0338262 A1 | 10/2020 | Kamen et al. | |

FOREIGN PATENT DOCUMENTS

| | | | |
|---|---|---|---|
| EP | 3000497 | A1 | 1/2019 |
| FR | 2096275 | A5 | 2/1972 |
| GB | 357139 | A | 9/1931 |
| GB | 810488 | A | 3/1959 |
| JP | 2009523535 | A | 6/2009 |
| JP | 2019525276 | A | 9/2019 |
| WO | 2007084214 | A1 | 7/2007 |
| WO | 2007092618 | A2 | 8/2007 |
| WO | 2019195521 | A1 | 10/2019 |
| WO | 2019213493 | A1 | 11/2019 |
| WO | 2019246381 | A1 | 12/2019 |
| WO | 2021011738 | A1 | 1/2021 |

OTHER PUBLICATIONS

International Search Report and Written Opinion for the International Patent Application No. PCT/US2021/047695, mailed Jan. 31, 2022, 26 pages.

International Search Report and Written Opinion for the International Patent Application No. PCT/US21/064056, mailed Apr. 4, 2022, 12 pages.

Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/blob/199ef86a900adf4b3d9c32f605eb11047bd3d62f/docs/EN/Module/module.rst [retrieved on Apr. 11, 2022] the whole document.

International Search Report and Written Opinion for the International Patent Application No. PCT/US22/018700, mailed Jun. 7, 2022, 13 pages.

Legacy Med Search, Insulet Enrolls First Patients in Clinical Trial for Omnipod, Sep. 16, 16, available at URL: https://legacymedsearch.com/insulet-enrolls-first-patients-in-clinical trial-for-omnipod-artificial-pancreas-system/.

* cited by examiner

FLUID DELIVERY PUMP VALVE ASSEMBLY

RELATED APPLICATIONS

This application claims the benefit of U.S. Provisional Patent Application No. 63/171,813, filed Apr. 7, 2021, the contents of which are incorporated herein by reference in their entirety.

FIELD OF THE INVENTION

The present disclosure generally relates to a pump for infusing a patient with a fluid, for example, a pump arranged within a wearable medicament delivery system, and, in particular, a multi-state valve for controlling the flow of the fluid through the pump.

BACKGROUND

Healthcare providers may prescribe patients wearable devices for delivering fluids, such as liquid medicaments, as part of a treatment regimen. Non-limiting examples of medicaments may include chemotherapy drugs, hormones (for instance, insulin), pain relief medications, and other types of liquid-based drugs. In general, wearable medicament delivery devices are relatively small form factors that may be adhered to the skin of the patient, with a reservoir to hold the medicament. The device may include a needle or cannula fluidically coupled to the reservoir and extending from the device and into the skin of the patient. A pump may operate to force the fluid from the reservoir, through a fluid path, and out through the needle and into the patient. A control system, with hardware and/or software elements, may be arranged within the device to manage medicament delivery and other device features. The control system may operate alone or in combination with an external computing device, such as a patient smartphone, healthcare provider computer, and/or the like.

Minimizing the footprint of a wearable medicament delivery device makes the device less obtrusive to the patient and improves the overall user experience. Accordingly, developers are consistently under pressure to reduce the size of operating components, while increasing the features (for example, monitoring patient physiological information, increasing automation, and/or the like) while limiting power demands. In order to achieve a smaller and more compact device, components are required to be smaller and more compact. For example, current pumping mechanisms include a valve switch to allow a user to fill the reservoir and to dispense a medicament. The valve must be shut while the user fills the reservoir, and open when the pump begins working. The valve must also differentiate between filling and dispensing of the pump. This entails three states for the valve, for example, closed, open for filling, and open for dispensing. Accordingly, conventional pump systems are not able to efficiently and effectively manage fluid flow within a device while meeting the space and energy demands of devices that are desired by patients.

Therefore, there is a need for an improved pumping mechanism for a wearable medicament delivery device that can be made compact and energy efficient while achieving a desired dosage accuracy.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In accordance with various features of the present disclosure is a fluid pump system for a wearable fluid delivery device. The fluid pump system may include a pump chamber to store a fluid, a fluid path in fluid communication with the pump chamber and a reservoir, a fluid path valve operative to control a state of the fluid path, the fluid path valve comprising a fixed portion and a movable portion, and a shaft configured to move along the fixed portion to engage the movable portion responsive to a force imparted by an actuator, the movable portion comprising an offset to deflect a force of the shaft to cause the movable portion to pivot from one of a first position or a second position to the other of the first position or the second position responsive to being engaged by the shaft to change the state of the fluid path.

In some embodiments of the fluid pump system, the wearable fluid delivery device may be configured to deliver a medicament to a patient, the medicament comprising insulin. In various embodiments of the fluid pump system, the fixed portion may include a V-feature having a substantially V-shape. In some embodiments of the fluid pump, the movable portion may include a bistable mechanism.

In exemplary embodiments of the fluid pump system, the state of the fluid path may include one of a fluid delivery state to deliver the fluid to the patient from the pump chamber or a fluid fill state to fill the pump chamber from a reservoir in fluid communication with the fluid path.

In various embodiments of the fluid pump system, the actuator may include a shape memory alloy. In some embodiments of the fluid pump, the offset may include a substantially triangular projection extending from the movable portion. In various embodiments of the fluid pump system, the fluid pump may include a spring configured to bias the shaft in a direction toward the movable portion in the absence of the force of the actuator. In exemplary embodiments of the fluid pump system, the shaft may include a detent arm.

In some embodiments of the fluid pump system, the movable portion may be associated with a first magnet attracted to a portion of the fixed portion to maintain the movable portion in contact with the fixed portion on a closed side of the fluid path valve until the shaft engages the movable portion to pivot the movable portion. In various embodiments of the fluid pump system, the V-feature may include at least one channel for shaft to travel during operation of the fluid path valve. In some embodiments of the fluid pump system, the at least one channel may include a sloped channel with at least one drop-off element to prevent the shaft from engaging an inner wall of the movable portion when traveling toward a central V-section of the V-feature.

In accordance with various features of the present disclosure is a fluid delivery device that may include a reservoir to store a fluid, a needle to infuse the fluid into a patient, and a fluid pump to pump the fluid through the needle. The fluid pump may include a pump chamber to store a fluid, a fluid path in fluid communication with the pump chamber and a reservoir, a fluid path valve operative to control a state of the fluid path, the fluid path valve comprising a fixed portion and a movable portion, and a shaft configured to move along the fixed portion to engage the movable portion responsive to a force imparted by an actuator, the movable portion comprising an offset to deflect a force of the shaft to cause the movable portion to pivot from one of a first position or a second position to the other of the first position or the second position responsive to being engaged by the shaft to change the state of the fluid path.

In some embodiments of the wearable fluid delivery device, the fluid may include insulin. In various embodiments of the wearable fluid delivery device, the fixed portion may include a V-feature having a substantially V-shape. In some embodiments of the wearable fluid delivery device, the movable portion may include a bistable mechanism.

In exemplary embodiments of the wearable fluid delivery device, the state of the fluid path may include one of a fluid delivery state to deliver the fluid to the patient from the pump chamber or a fluid fill state to fill the pump chamber from a reservoir in fluid communication with the fluid path.

In various embodiments of the wearable fluid delivery device, the actuator may include a shape memory alloy. In some embodiments of the wearable fluid delivery device, the offset may include a substantially triangular projection extending from the movable portion. In various embodiments, the wearable fluid delivery device may include a spring configured to bias the shaft in a direction toward the movable portion in the absence of the force of the actuator. In exemplary embodiments of the wearable fluid delivery device, the shaft may include a detent arm.

In some embodiments of the wearable fluid delivery device, the movable portion may be associated with a first magnet attracted to a portion of the fixed portion to maintain the movable portion in contact with the fixed portion on a closed side of the fluid path valve until the shaft engages the movable portion to pivot the movable portion. In various embodiments of the wearable fluid delivery device, the V-feature may include at least one channel for the shaft to travel during operation of the fluid path valve. In some embodiments of the wearable fluid delivery device, the at least one channel may include a sloped channel with at least one drop-off element to prevent the shaft from engaging an inner wall of the movable portion when traveling toward a central V-section of the V-feature.

In accordance with various features of the present disclosure is a bistable push-push mechanism fluid path that may include a fluid path valve configured to be arranged in one of a fluid fill state or a fluid delivery state, the fluid path valve comprising a non-movable V-feature configured to engage a detent, the detent to move along a path formed by the V-feature toward a pivotable bistable mechanism in response to a force imparted by a spring biasing the detent toward the bistable mechanism in the absence of a force imparted by an actuator (or vice versa), wherein the movable portion comprises an offset to deflect movement of the detent to cause the bistable mechanism to pivot from one of the fluid fill state to the fluid delivery state to the other of the fluid fill state or the fluid delivery state responsive to being engaged by the detent.

In accordance with various features of the present disclosure is a method of manufacturing a wearable medicament delivery device. The method may include providing a reservoir configured to hold the medicament and providing a pump system operatively coupled to the reservoir. The pump system may include a pump chamber to store a fluid, a fluid path in fluid communication with the pump chamber and the reservoir, a fluid path valve operative to place a fluid path into one of a fluid fill state or a fluid delivery state, the fluid path valve comprising a fixed portion and a movable portion, and a shaft configured to move along the fixed portion to engage the movable portion responsive to a force imparted by an actuator, the movable portion comprising an offset to deflect a force of the shaft to cause the movable portion to pivot from one of the fluid fill state to the fluid delivery state to the other of the fluid fill state to the fluid delivery state responsive to being engaged by the shaft to change the state of the fluid path. The method may further include providing a needle configured to receive the medicament from the pump system when the fluid path valve is in the fluid delivery state for delivery to a patient.

Figure 1:
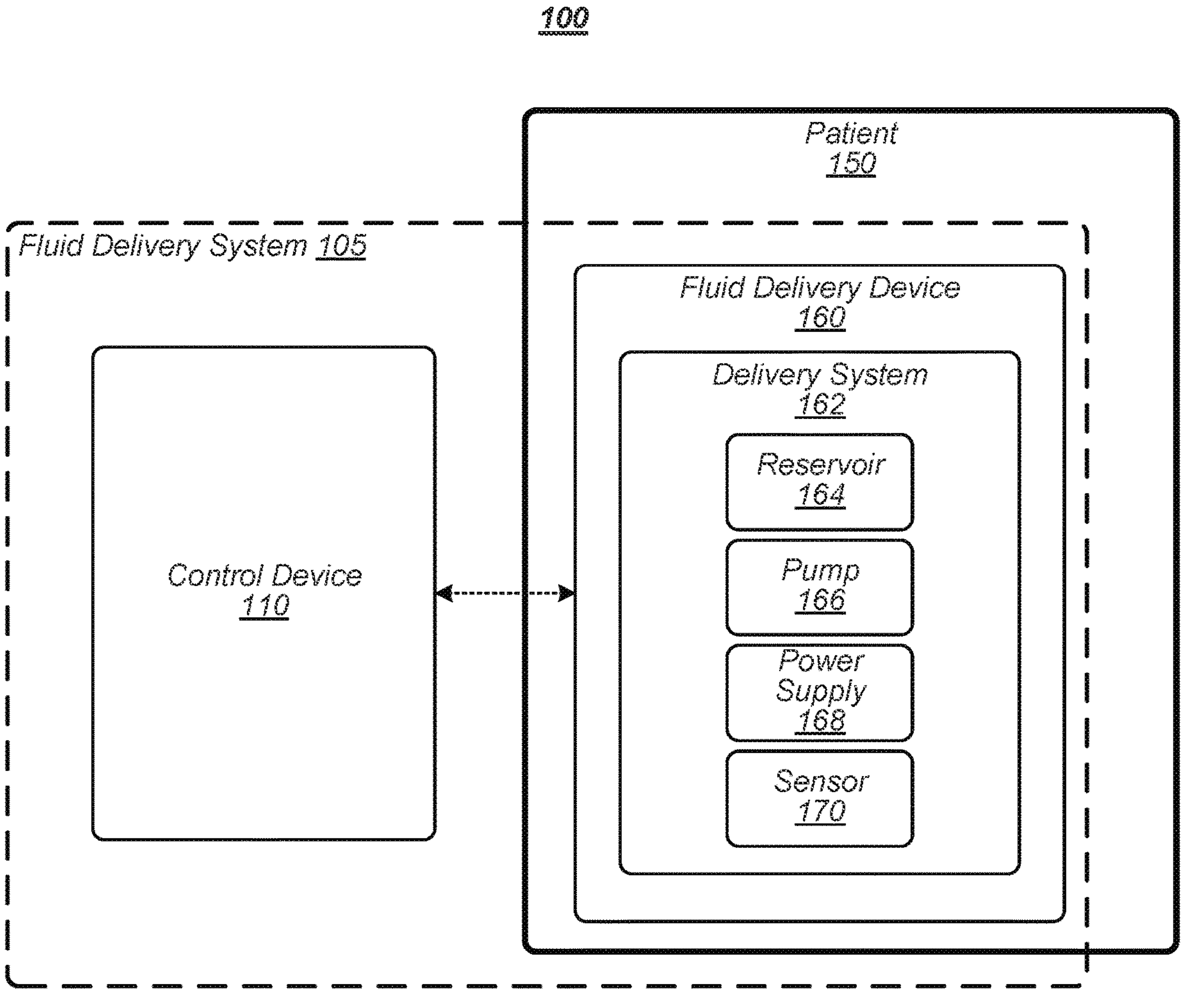
FIG. 1 illustrates an exemplary operating environment in accordance with the present disclosure.

The drawings are not necessarily to scale. The drawings are merely representations, not intended to portray specific parameters of the disclosure. The drawings are intended to depict example embodiments of the disclosure, and therefore should not be considered as limiting in scope. In the drawings, like numbering represents like elements

DETAILED DESCRIPTION

The described technology generally relates to a wearable fluid delivery device for delivering a fluid to a patient. In some embodiments, the fluid may be or may include a medicament. The wearable fluid delivery device may include a reservoir for holding the fluid, a fluid path in fluid communication with the reservoir, a needle in fluid communication with the fluid path to deliver the fluid to the patient wearing the wearable fluid delivery device, and a fluid delivery pump configured to force the fluid from the reservoir, through the fluid delivery path, and into the patient via the needle.

In some embodiments, a fluid path valve or switch may be within, or in fluid communication with, the fluid path. The fluid path valve may be configured to alternate between multiple states or positions to configure the flow of the fluid through the fluid path. For example, operation of the fluid delivery pump may be configured to alternate between filling a pump chamber with fluid from the reservoir and pumping the fluid from the pump chamber into the patient. The fluid path valve may be set into a first state for filling the pump chamber and a second state to allow operation of the pump to move the fluid from the pump chamber and into the patient. In various embodiments, the fluid path valve may be a bistable valve having two stable positions. In exemplary embodiments, the fluid path valve may be or may include a "push-push" mechanism configured to actuate between at least two states. In various embodiments, the fluid path valve may be or may include a bistable push-push mechanism. In general, bistable push-push mechanism may enter two possible states, alternating between each state with each "push" or actuation. For example, a bistable push-push mechanism may enter a first state responsive to a first actuation, a second actuation may cause the bistable push-push mechanism to enter a second state, a third actuation may cause the bistable push-push mechanism to re-enter the first state, a fourth actuation may cause the bistable push-push mechanism to re-enter the second state, and so on.

In a conventional fluid delivery device, a pump, such as a reciprocating pump, may require a fluid path that alternates between filling a pump chamber with fluid from a reservoir, and pumping fluid from the chamber into the patient. One example technique to accomplish this is by incorporating an independent actuator to alternate the system between these two states, which would decrease the required load on the pumping actuators. A shape-memory alloy (SMA) wire or other actuator may be used to drive the system; however, one actuator is only able to control one direction of movement in the system, which would be ineffective or greatly increase energy consumption if the actuator needed to hold the fluid path in one position.

Accordingly, a mechanism to reliably alternate between two or more positions is required. In some embodiments, for example, a detent (or detent arm, arm, rod, shaft, pin, rod, push-push element, and/or the like) actuated by an actuator (for example, via an SMA wire and/or a spring) may be placed inside a fluid pathway (for instance, as a fluid pathway valve) that can alternate between two configurations, and attaching them to the needle in the pump, the system may reliably rest in two positions (for instance, a fluid fill state and a fluid delivery state). In some embodiments, the general shape of the path may be or may substantially be a "V" shape, for example, where the inside will be attached to a bistable mechanism that is fixed at the center (see, for example, FIGS. 4B and 5). In various embodiments, an inner corner of the wall of the path may be offset from the outer corner, which may change based on the configuration of the bistable mechanism. By offsetting the corner of the inner wall, the detent may reliably move to one side of the V-shaped path. The configuration of the bistability may be altered when the detent contacts it and causes it to deflect at each of the top points of the V-shaped path (see, for example, FIG. 5).

FIG. 1 illustrates an example of an operating environment 100 that may be representative of some embodiments. As shown in FIG. 1, operating environment 100 may include a fluid delivery system 105. In various embodiments, fluid delivery system 105 may include a control or computing device 110 that, in some embodiments, may be communicatively coupled to a fluid delivery device 160. Computing device 110 may be or may include one or more logic devices, including, without limitation, a server computer, a client computing device, a personal computer (PC), a workstation, a laptop, a notebook computer, a smart phone, a tablet computing device, a personal diabetes management (PDM) device, and/or the like. Embodiments are not limited in this context.

Fluid delivery device 160 may be or may include a wearable automatic fluid delivery device directly coupled to patient 150, for example, directly attached to the skin of the user via an adhesive and/or other attachment component.

In some embodiments, fluid delivery device 160 may be or may include a medicament delivery device configured to deliver a liquid medicament, drug, therapeutic agent, or other medical fluid to a patient. Non-limiting examples of medicaments may include insulin, GLP-1, pramlintide, glucagon, pain relief drugs, hormones, blood pressure medicines, morphine, methadone, chemotherapy drugs, proteins, antibodies, a co-formulation of more than one of the foregoing, and/or the like.

In some embodiments, fluid delivery device 160 may be or may include an automatic insulin delivery (AID) device configured to deliver insulin (and/or other medication) to patient 150. For example, fluid delivery device 160 may be or may include a device the same or similar to an OmniPod® device or system provided by Insulet Corporation of Acton, Mass., United States, for example, as described in U.S. Pat. Nos. 7,303,549; 7,137,964; and/or 6,740,059, each of which is incorporated herein by reference in its entirety. Although an AID device and insulin are used in examples in the present disclosure, embodiments are not so limited, as fluid delivery device 160 may be or may include a device capable of storing and delivering any fluid therapeutic agent, drug, medicine, hormone, protein, antibody, and/or the like.

Fluid delivery device 160 may include a delivery system 162 having a number of components to facilitate automated delivery of a fluid to patient 150, including, without limitation, a reservoir 164 for storing the fluid, a pump 166 for transferring the fluid from reservoir 164, through a fluid path or conduit, and into the body of patient 150, and/or a power supply 168. Fluid delivery device 160 may include at least one penetration element (not shown) configured to be inserted into the skin of the patient to operate as a conduit between reservoir 164 and patient 150. For example, penetration element may include a cannula and/or a needle. Embodiments are not limited in this context, for example, as delivery system 162 may include more or fewer components.

In some embodiments, fluid delivery device 160 may include at least one sensor 170 operative to detect, measure, or otherwise determine various physiological characteristics of patient 150. For example, sensor 170 may be or may include a continuous glucose monitoring (CGM) sensor operative to determine blood glucose measurement values of patient 150. In another example, sensor may be or may include a heart rate sensor, temperature sensor, and/or the like.

In various embodiments, fluid delivery device 160 may be a closed-loop fluid delivery system using sensor 170 as an internal monitor to track patient information, either directly or via control device 110, to delivery system 162 to formulate delivery of a fluid to patient 150 via the penetration element.

In some embodiments, computing device 110 may be a smart phone, PDM, or other mobile computing form factor in wired or wireless communication with fluid delivery device 160. For example, computing device 110 and Fluid delivery device 160 may communicate via various wireless protocols, including, without limitation, Wi-Fi (i.e., IEEE 802.11), radio frequency (RF), Bluetooth™, Zigbee™, near field communication (NFC), Medical Implantable Communications Service (MICS), and/or the like. In another example, computing device 110 and fluid delivery device 160 may communicate via various wired protocols, including, without limitation, universal serial bus (USB), Lightning, serial, and/or the like. Although computing device 110 (and components thereof) and fluid delivery device 160 are depicted as separate devices, embodiments are not so limited. For example, in some embodiments, computing device 110 and fluid delivery device 160 may be a single device. In another example, some or all of the components of computing device 110 may be included in fluid delivery device 160. For example, Fluid delivery device 160 may include processor circuitry, memory unit, and/or the like. In some embodiments, each of computing device 110 and fluid delivery device 160 may include a separate processor circuitry, memory unit, and/or the like capable of facilitating insulin infusion processes according to some embodiments, either individually or in operative combination. Embodiments are not limited in this context.

Figure 2:
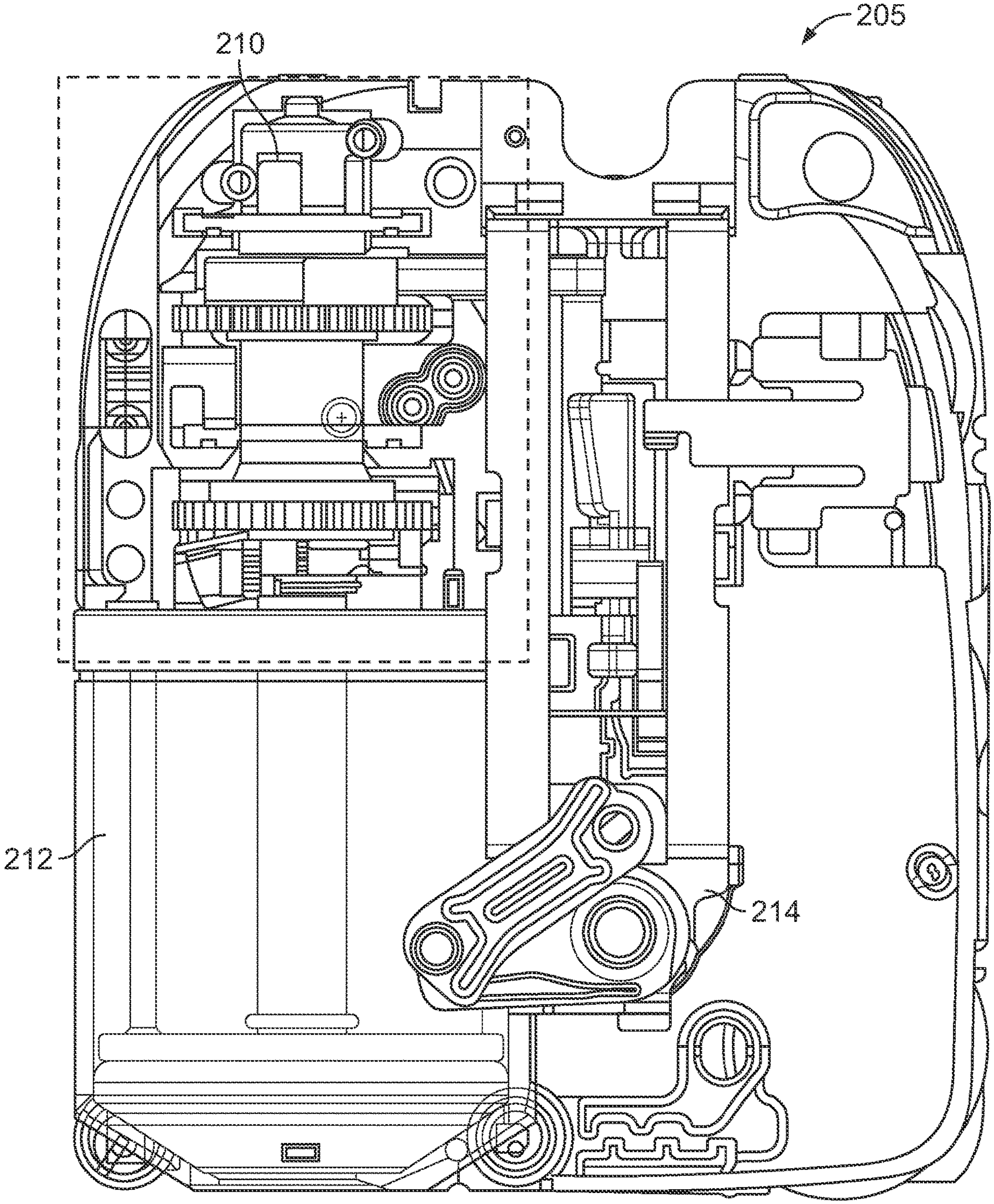
FIG. 2 illustrates an exemplary wearable fluid delivery device in accordance with the present disclosure.

FIG. 2 illustrates an exemplary wearable fluid delivery device in accordance with the present disclosure. In particular, FIG. 2 depicts a top-down view of a wearable fluid delivery device 205. As shown in FIG. 2, a wearable fluid delivery device 205 may include multiple systems to store and delivery a fluid to a patient. Fluid delivery device 205 may include one or more housings configured to enclose the multiple systems. In some embodiments, wearable fluid delivery device 205 may include a pump 210. In various embodiments, pump 210 may be or may include a reciprocating pump (see, for example, FIGS. 3, 4A, and 4B). In exemplary embodiments, wearable fluid delivery device 205 may include a reservoir 212 for storing a fluid. Reservoir may be in fluid communication with pump 210 for delivering the fluid to patient via needle 214.

In various embodiments, pump 210 may be a multi-dose reciprocating pump. In some embodiments, pump 210 may be configured to deliver about 0.25 microliters per pulse. In exemplary embodiments, pump 210 may have a footprint of about 23 millimeters (mm)×28 mm×12 mm.

Figure 3:
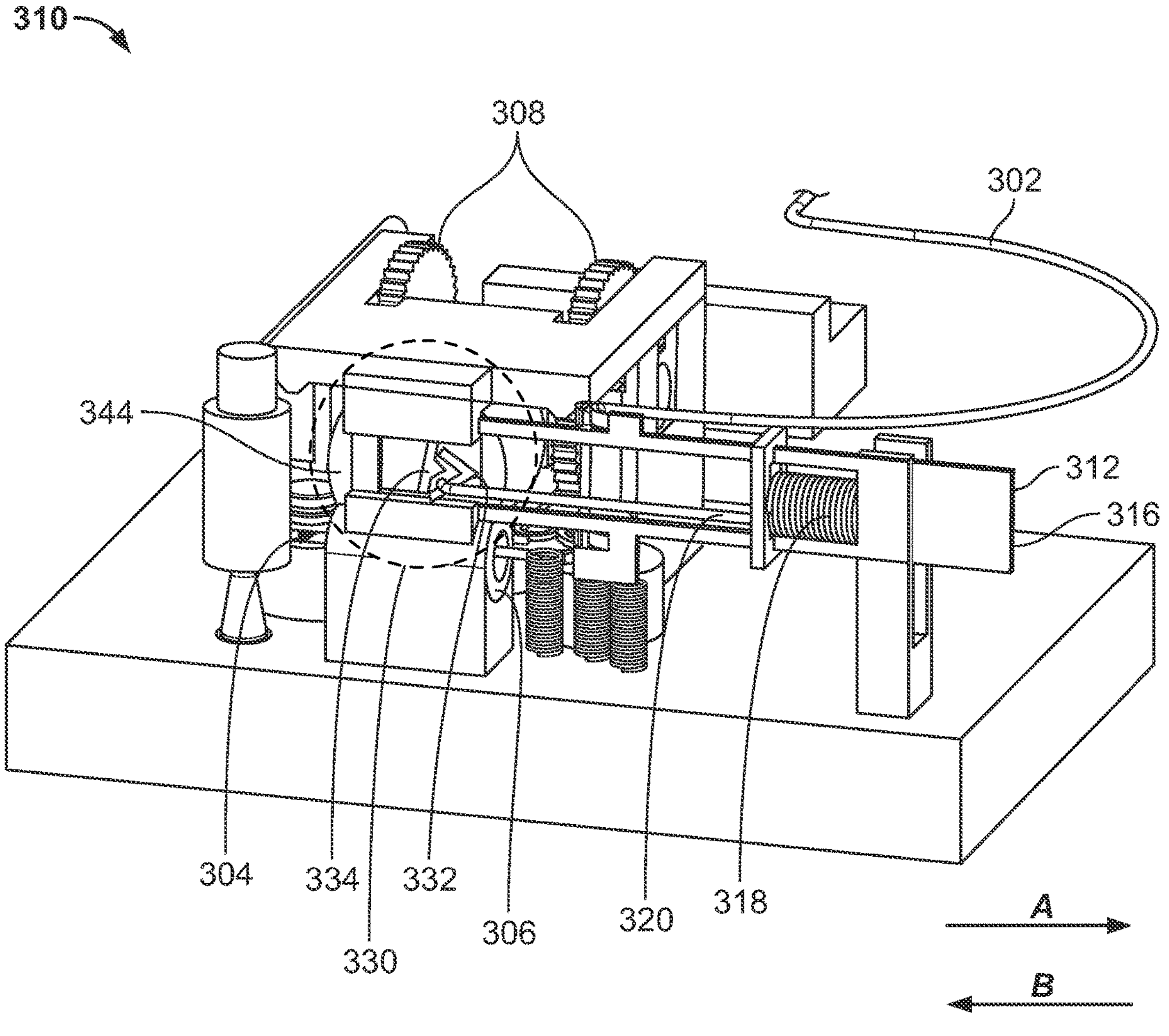
FIG. 3 illustrates an embodiment of a fluid delivery pump in accordance with the present disclosure.

FIG. 3 illustrates an embodiment of a fluid delivery pump in accordance with the present disclosure. As shown in FIG. 3, a fluid delivery pump 310 may include a ratchet or ratchet wheels 308 operably coupled to a snail cam (not shown, see, for example, FIG. 4A), a reservoir inlet 304 fluidically coupled to a reservoir (not shown), and a patient outlet 306 fluidically coupled to a needle 302. Rotation of ratchet wheels 308 may cause fluid to flow from the reservoir to a pump chamber 344 or through needle 302 to patient depending on a flow path state, for instance, whether the pump is in a chamber fill state (fluid fill state) or a patient infusion state (fluid delivery state), respectively.

A fluid path valve 330 may be configured to switch the flow path state of pump 310 from a first state (for instance, a fluid fill state or chamber fill state) to a second state (for instance, a fluid delivery state or patient infusion state).

In some embodiments, fluid path valve 330 may include a fixed portion 332 and a movable portion 334. In some embodiments, fixed portion 332 may be an outer wall of fluid path valve 330. In various embodiments, fixed portion 332 may be a V-feature. In exemplary embodiments, movable portion 334 may pivot about a pivot point. In various embodiments, movable portion 334 may be a pivotable inner wall of fluid path valve 330. In some embodiments, movable portion 334 may be or may include a bistable push-push mechanism (push-push mechanism, bistable mechanism, or inner wall).

A detent (or shaft, rod, pin, and/or the like) 320 may be configured to engage V-feature 332 and/or bistable mechanism 334 to set the state of fluid path valve 330. In some embodiments, detent 320 may be coupled to a bracket 312 or other structure. In various embodiments, forces intended to move detent 320 may be wholly or partially imparted on bracket 312 to move detent 320. In other embodiments, forces intended to move detent 320 may be wholly or partially imparted directly on detent 320.

Although element 334 is described in examples in the present disclosure as a bistable mechanism, push-push mechanism, or bistable push-push mechanism, embodiments are not so limited. For example, element 334 may be or may include other mechanisms besides a bistable mechanism, push-push mechanism, or bistable push-push mechanism. In another example, element 334 is not limited to a bistable mechanism, push-push mechanism, or bistable push-push mechanism or may be a push-push mechanism with more than two states. Rather, use of examples of a bistable mechanism, push-push mechanism, or bistable push-push mechanism are intended to provide illustrative functional embodiments of element 334. Accordingly, element 334 may be or may include any mechanism, element, structure, and/or the like capable of operating according to some embodiments.

Although element 332 is described in examples in the present disclosure as a V-feature, embodiments are not so limited. For example, element 332 is not required to be "V" shaped. Rather, use of a "V" shape or the term V-feature are not intended to be limiting but are intended to provide illustrative functional embodiments of element 332. Accordingly, element 334 may be or may include any mechanism, element, structure, and/or the like, with various different shapes, capable of operating according to some embodiments.

In some embodiments, forces intended to move detent 320 may be wholly or partially imparted on bracket 312 to move detent 320 may be actuated or moved by an actuator 316. In various embodiments, actuator may be or may include an SMA wire operably coupled to detent 320 and/or a bracket 312. In exemplary embodiments, a spring 318 may be operably coupled to detent 320 and/or a bracket 312. In some embodiments, actuator 316 may impart a force on detent 320 to move detent in direction A (for instance, away from bistable mechanism 334). In some embodiments, actuator 316 may impart a force on detent 320 to move detent in direction B (for instance, toward bistable mechanism 334).

In some embodiments, a spring 318 may operate to bias detent 320, for example, in the direction of arrow B. Accordingly, if actuator 316 is not providing a force to move detent 320 in the direction of arrow A, detent 320 may be biased in the direction of arrow B. For example, an SMA wire actuator 316 may be activated to move detent 320 in the direction of arrow A. Relaxation of SMA wire actuator 316 may cause detent 320 to move back in the direction of arrow B. In this manner, fluid path valve 330 may be switched between fluid path states (see, for example, FIGS. 6A-6E).

In some embodiments, actuator 316, and other components of pump 310, may be actuated via hardware and/or software of a wearable fluid delivery device and/or an external computing device communicatively coupled to wearable fluid delivery device (see, for example, FIG. 1).

Figure 4A:
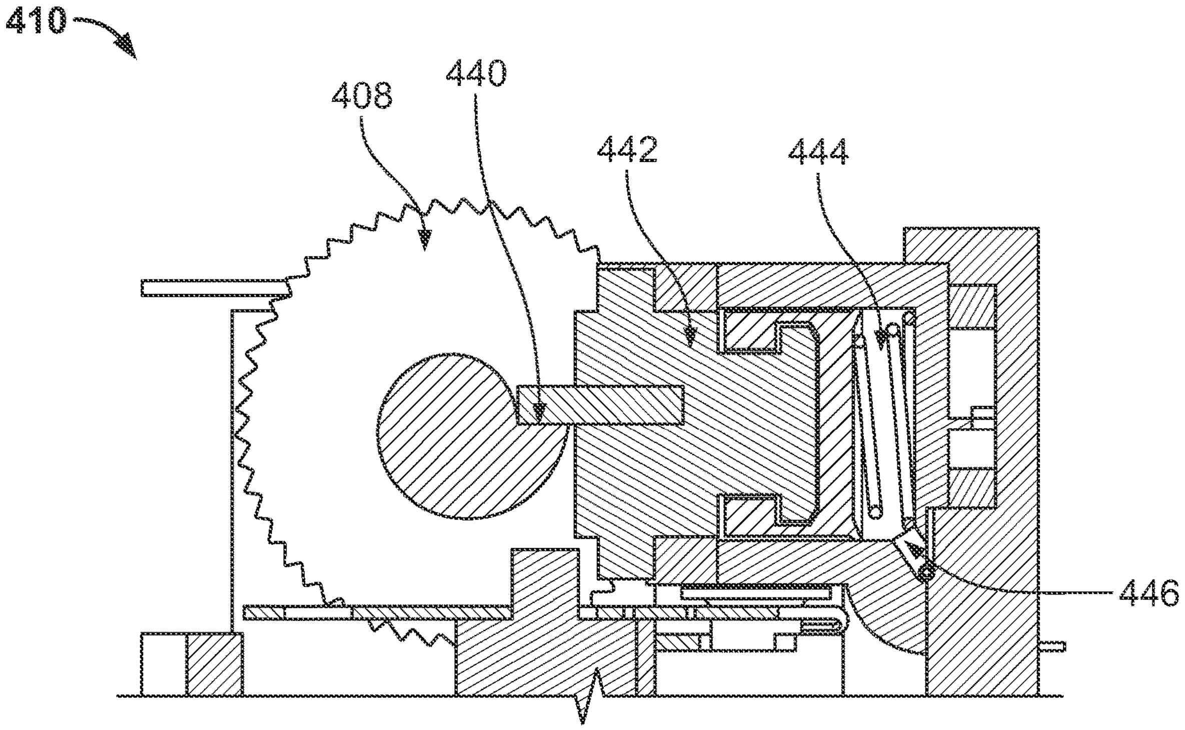
FIGS. 4A and 4B illustrate an embodiment of a fluid delivery pump in accordance with the present disclosure.
Figure 4B:
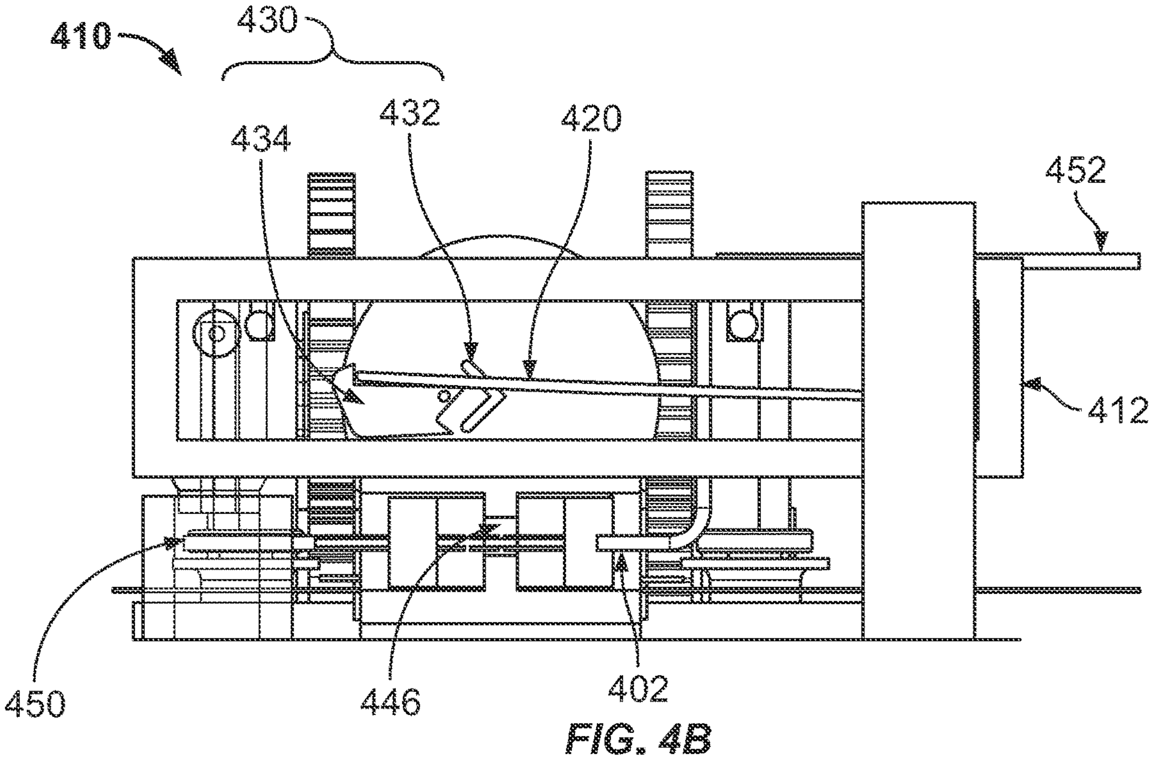

FIGS. 4A and 4B illustrate an embodiment of a fluid delivery pump in accordance with the present disclosure. More specifically, FIGS. 4A and 4B show a cross-sectional side view and a front view, respectively, of a fluid delivery pump 410. In some embodiments, fluid delivery pump 410 may be a reciprocating pump.

As shown in FIGS. 4A and 4B, pump 410 may include a ratchet wheel 408, a snail cam 440, a piston 442, and a chamber 444. In some embodiments, a fluid path of pump 410 may include a reservoir entrance to needle 450, a chamber/needle passthrough 446, and a needle 402 with a needle exit 452. A fluid path valve 430 may include a V-feature 432 and a bistable mechanism 434.

During operation of pump 410, fluid path valve 430 may be placed in a chamber fill state, for example in which a reservoir (not shown) is open to chamber 444 and closed to needle 402 (and patient). Rotation of ratchet 408 may rotate past the drop off of snail cam 440 and piston 442 may reset to chamber 444. Fluid path valve 430 may be switched to the patient infusion state, for example, in which chamber inlet 450 is closed to reservoir and needle 402 is open to chamber 444. In the patient infusion state, rotation of ratchet 408 may cause fluid to be pumped from chamber 444, through needle 402, and into the patient.

Figure 5:
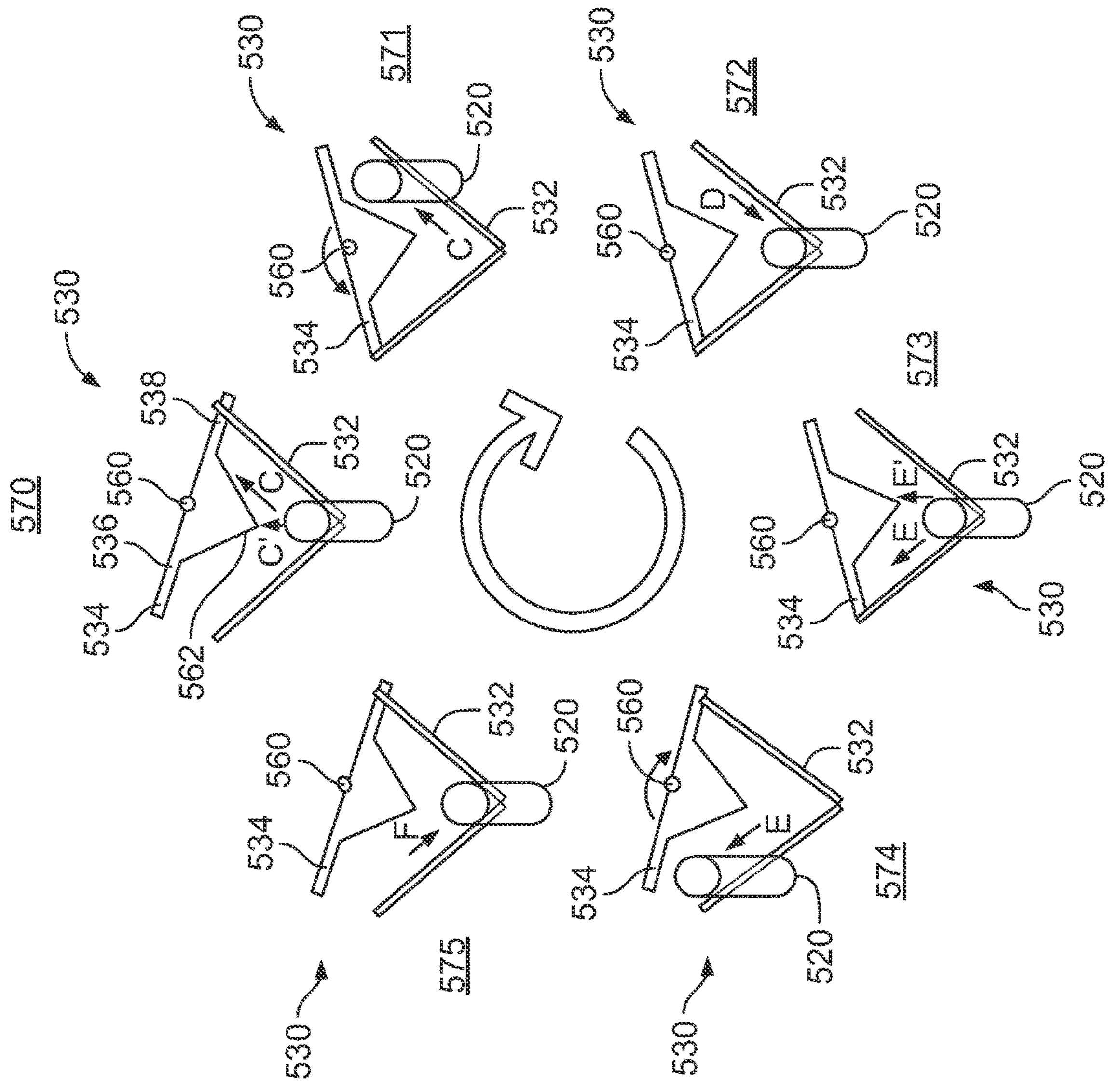
FIG. 5 illustrates an embodiment of a fluid path valve in accordance with the present disclosure.

FIG. 5 illustrates an embodiment of a fluid path valve in accordance with the present disclosure. More specifically, FIG. 5 depicts steps 570-575 of fluid path valve 530 as fluid path valve 530 transitions between states. As shown in FIG. 5, fluid path valve 530 may include a fixed portion (or V-feature) 532 and a movable portion (or bistable mechanism) 534 operably coupled to a pivot element 560 configured to allow bistable mechanism 534 to pivot responsive to force provided by a shaft or detent 520. In some embodiments, V-feature 532 and bistable mechanism 534 may form a path, for example, with V-feature 532 being configured as a fixed outer wall of the path and bistable mechanism 534 being an inner wall of the path (that pivots on pivot element 560).

In some embodiments, V-feature 532 may include a path, groove, inset, slot, wall, or other structure that may guide detent 520, for example, responsive to forces imparted by an actuator and/or spring. In various embodiments, V-feature 532 may be offset or non-parallel and/or may include projections to cause detent 520 to deflect in a desired direction. In exemplary embodiments, bistable mechanism 534 may have an offset or projection 562 (for instance a tip of a triangular or substantially triangular portion) that may be offset to cause detent 520 to deflect in a desired direction. Projection 562 may form a first side, inner wall, extension, overhang, arm, or other structure 536 of bistable mechanism on a first side of projection 562 and a second side, inner wall, extension, overhang, arm, or other structure 538 on a second side of projection (first wall 536 and second wall 538 are only labeled in step 570 to limit the complexity of FIG. 5). Projection 562 may be offset to cause detent 520 to deflect in a desired direction to engage first wall 536 or second wall 538 to cause bistable mechanism to tilt, pivot, or otherwise move in a desired direction to change a state of fluid path valve 530.

At step 570, fluid path valve 530 may be in a first state (for example, a chamber fill state). Detent may be pulled in direction C' at step 570, for example, in response to an actuation by an SMA wire or other actuator (or conversely, due to the force of a biasing spring in the absence of actuation by an SMA wire). However, offset 562 (for instance, a triangular projection) of bistable mechanism 534 may be configured to cause detent 520 to deflect in direction C (for instance, to the right) and contact second wall 538. For example, as detent 520 is pulled up toward bistable mechanism, detent 520 may hit at or near the point of the triangular projection of offset 562, causing detent 520 to veer into direction C.

At step 571, detent 520 may contact bistable mechanism 534 on the right side (for instance, at second wall 538), causing bistable mechanism 534 to rotate counterclockwise. Fluid delivery valve may now be in a second state, such as a patient infusion state, after rotating to create an opening between V-feature 534 and second wall 538. At step 572, detent 520 may get pulled in direction D and come to a rest in a corner of V-feature 534.

At step 573, detent may be pulled in direction E', however, at this stage, the orientation of offset 562 of bistable mechanism 534 may cause detent 520 to deflect in direction E (for instance, to the left). At step 574, detent 520 may contact bistable mechanism 534 on the left side (for instance, at first wall 536), cause bistable mechanism 534 to rotate clockwise. At step 575, detent 520 may get pulled in direction F and come to a rest in a corner of V-feature 534.

Process of steps 570-575 may be repeated to switch the flow path from a first state (for instance, a chamber fill state) to a second state (for instance, a patient infusion state). For example, steps 571-573, in which V-feature 534 is open on the upper right side, may be a first state, and steps 570, 574, and 575, in which V-feature 534 is open on the upper left side may be a second state, or vice versa.

FIGS. 6A-6E illustrate operation states of an embodiment of a fluid delivery pump in accordance with the present disclosure. More specifically, FIGS. 6A-6E depict steps 670-678 of a fluid infusion process (for instance, including chamber fill and patient infusion processes), depicting a cross-sectional side view and a front view for a pump 610 according to some embodiments.

Figure 6A:
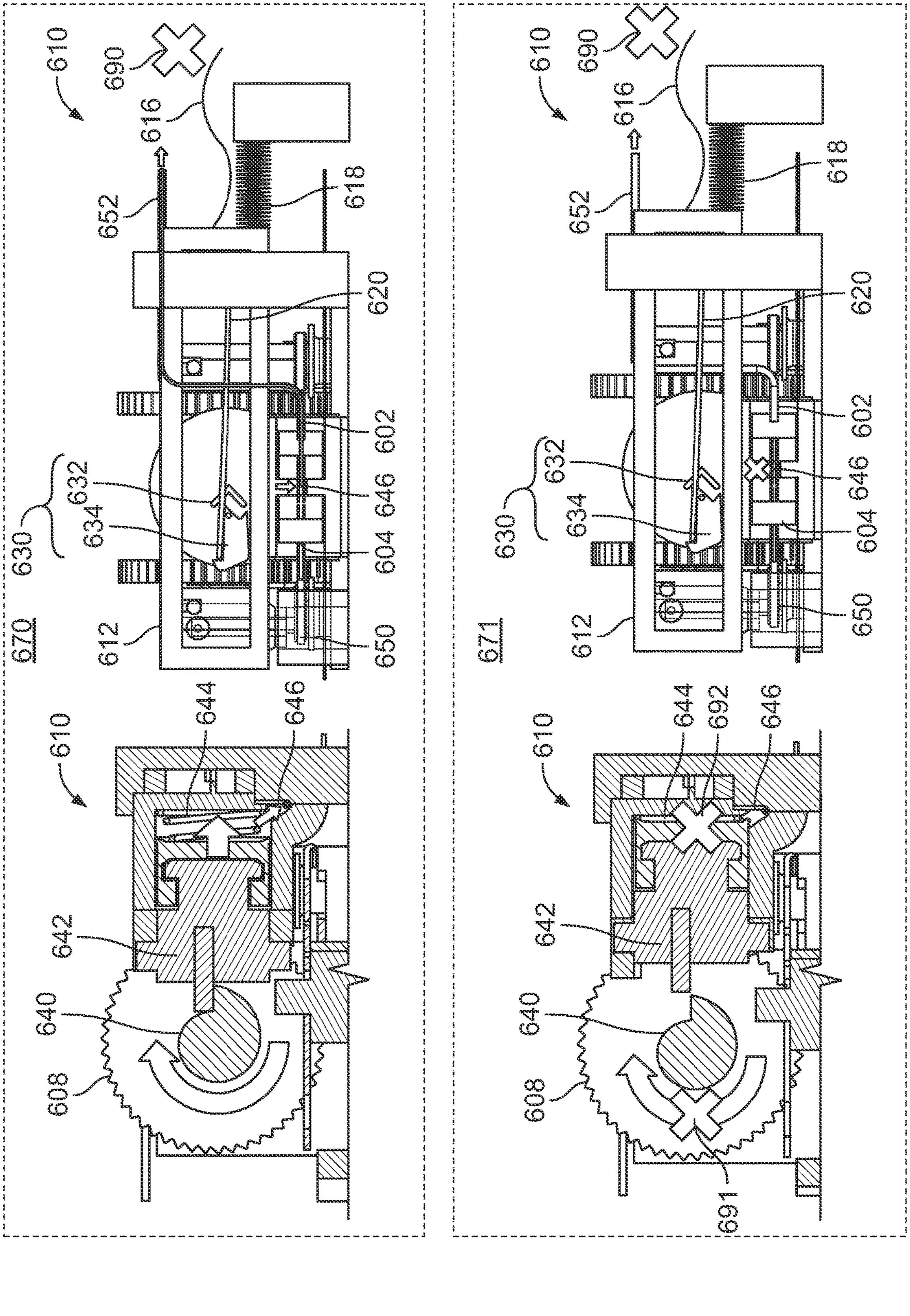
FIGS. 6A-6E illustrate operation states of an embodiment of a fluid delivery pump in accordance with the present disclosure.
Figure 6B:
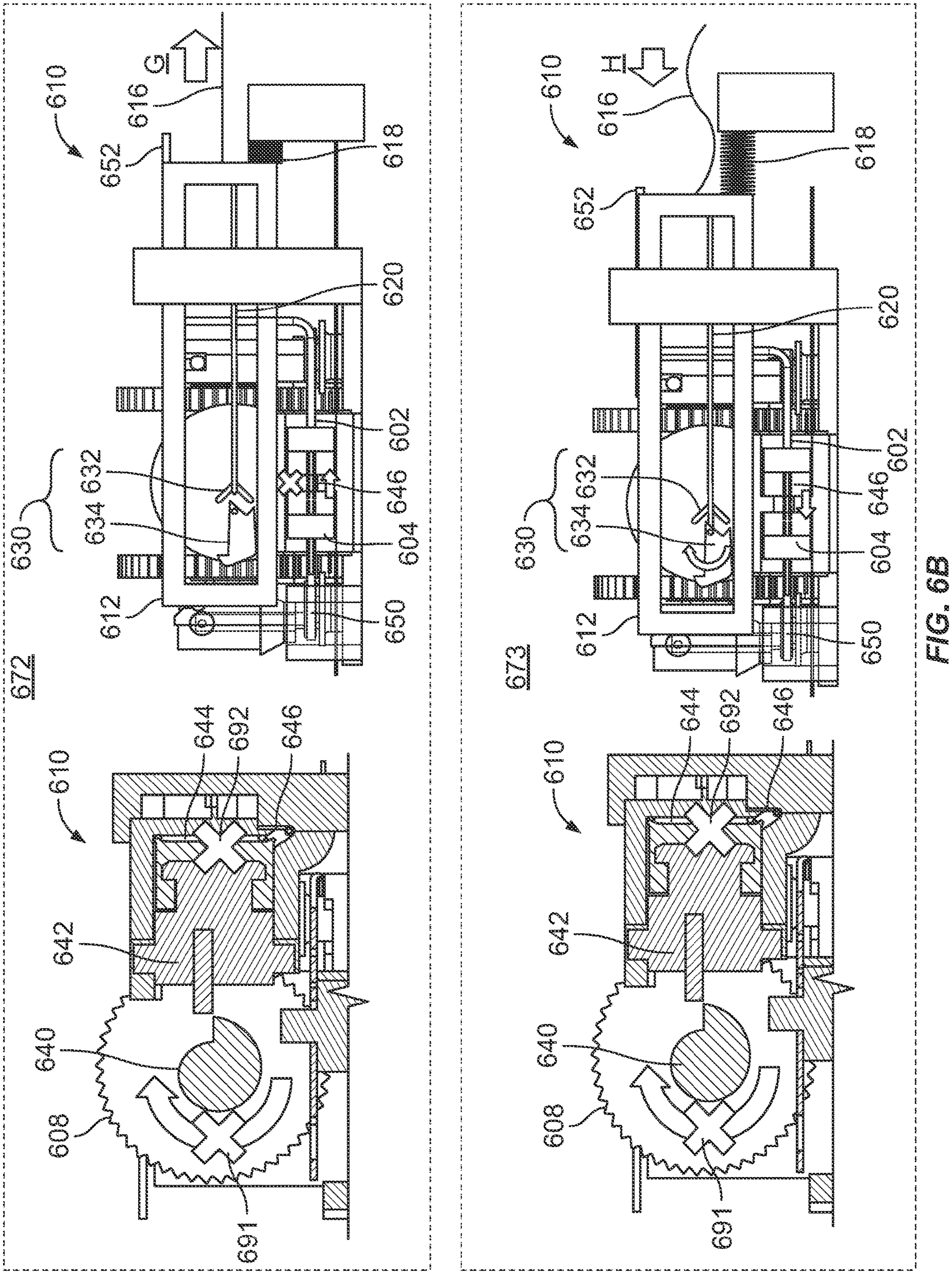
Figure 6C:
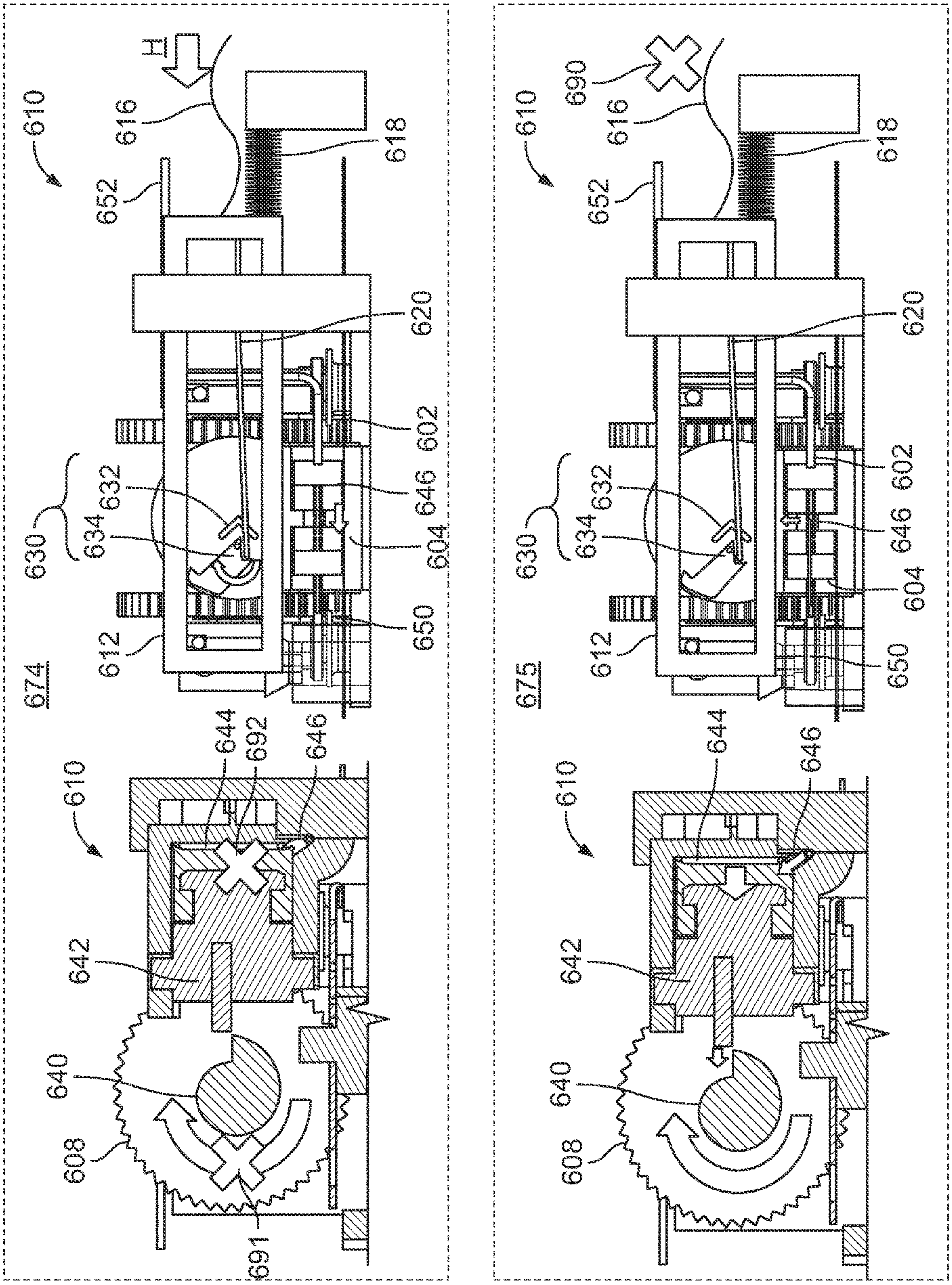
Figure 6D:
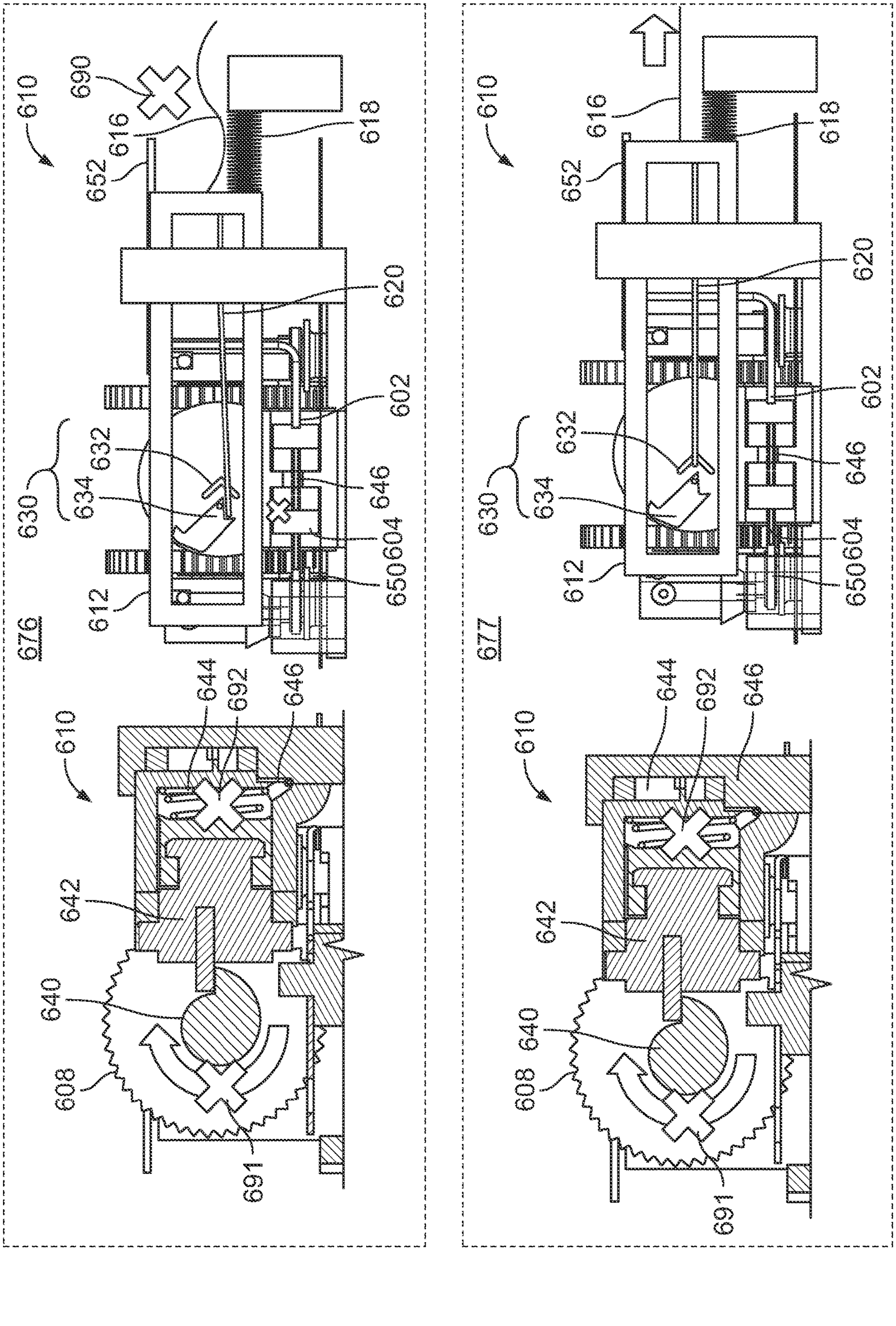
Figure 6E:
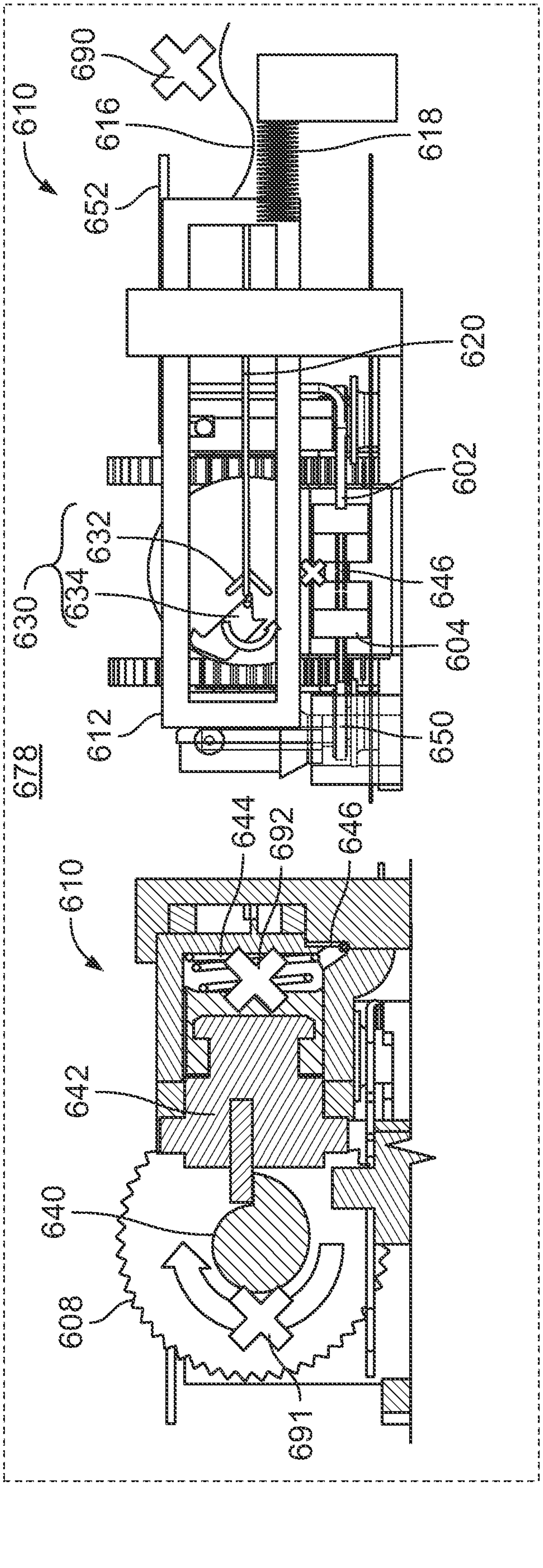

As shown in FIG. 6A, a pump 610 may include a ratchet 608, snail cam 640, piston 642 and chamber 644. In some embodiments, a fluid path of pump 610 may include a reservoir entrance to needle 650, a chamber/needle pass-through 646, and a needle 602 with a needle exit 652. A fluid path valve 630 may include a V-feature 632 and a bistable mechanism 634.

In some embodiments, a detent 620 may be operably coupled to a bracket 312/612. An actuator 616 may be operably coupled to bracket 312 to impart a force on detent 620. In some embodiments, actuator 616 may be or may include an SMA wire that, when activated, may pull detent 620. In exemplary embodiments, a spring 318/618 may be operably coupled to detent 320/620 and/or a bracket 312/612 to bias detent 320/620 (for instance, in the absence of a force by actuator 616).

At step 670, the fluid path is in a first position (for instance, a patient infusion position) such that rotation of ratchet wheel 608 may pump the fluid out of chamber 644 and into the patient. This infusion pulse may be repeated for multiple pulses, such as about 50 to about 100 pulses. Actuator 616 is deactivated, as indicated by X 690. At step 671, ratchet wheel 608 may stop (indicated by X 691 as the drop off of snail cam 640 approaches. In step 671, pump 610 may stop moving the fluid (as indicated by X 692) and the fluid path remains in the patient infusion position.

At step 672, SMA 616 is activated, pulling detent 620 in direction G. Detent 620 may center on V-feature 632 and the fluid path may move out of the patient infusion position. At step 673, SMA 616 is deactivated, initiating SMA release, causing detent 620 to move in direction H. Detent 620 may contact and cause rotation (for instance, clockwise rotation) of bistable mechanism 634. The fluid path may move into a second position (for instance, a chamber fill position).

At step 674, SMA release continues such that detent 620 continues moving in direction H. Detent 620 further rotates bistable mechanism 634 and moves the fluid path into the chamber fill position. At step 675, ratchet wheel 608 may rotate and piston 642 may fall off of the drop off of snail cam 640, creating a vacuum or negative pressure in chamber 644 that draws fluid from the reservoir, through 650 and into chamber 644.

At step 676, ratchet wheel 608 may stop moving and chamber 644 may be at least partially full of the fluid. The fluid path may be in a chamber fill (or non-infusion) position. At block 677, SMA 616 may be activated, pulling detent 620 in direction H. Detent 620 may center on V-feature 632 and the fluid path may move out of the chamber fill position. At step 678, SMA 616 may be deactivated and detent 620 may contact and rotate (for instance, counterclockwise) bistable mechanism 634. The fluid path may be moved into the patient infusion position.

Figure 7:
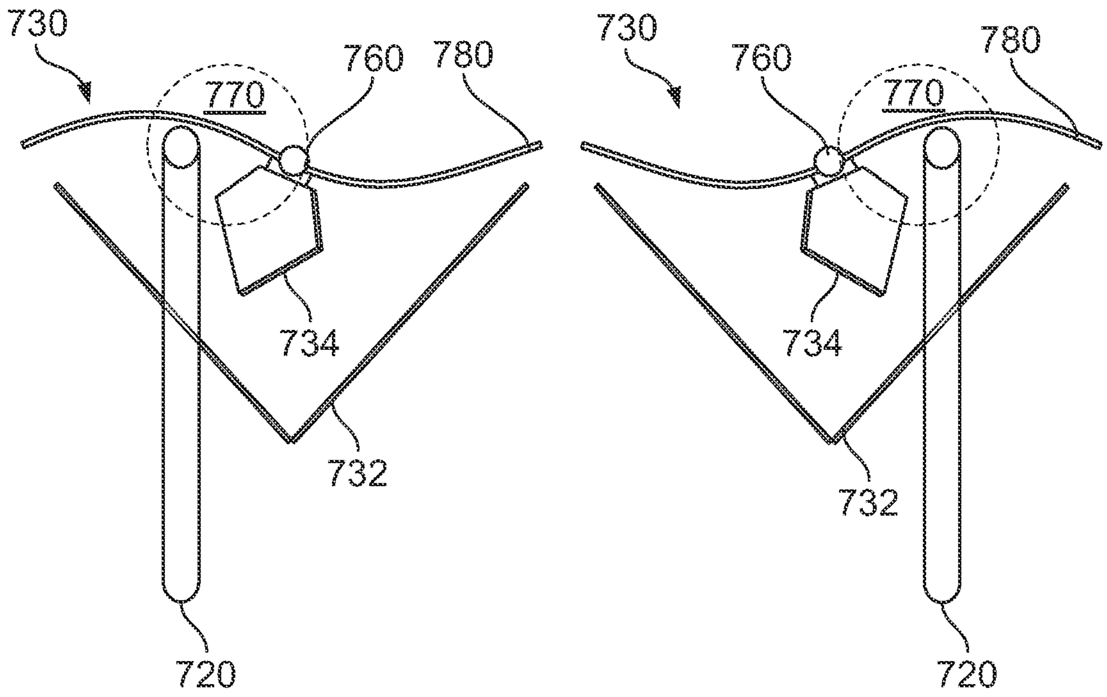
FIG. 7 illustrates an embodiment of a fluid path valve in accordance with the present disclosure.

FIG. 7 illustrates an embodiment of a fluid path valve in accordance with the present disclosure. As shown in FIG. 7, a fluid path valve 730 may include a V-feature 732 and a bistable mechanism 734. In some embodiments, bistable mechanism 734 may include a beam 780. In various embodiments, a shape of bistable mechanism 734 may be configured to reduce or even eliminate detent 720 from being caught, stuck, or otherwise trapped, either temporarily or permanently, in area 770 between bistable mechanism 734 and beam 780. This embodiment may be used in the system shown in earlier figures.

Figure 8:
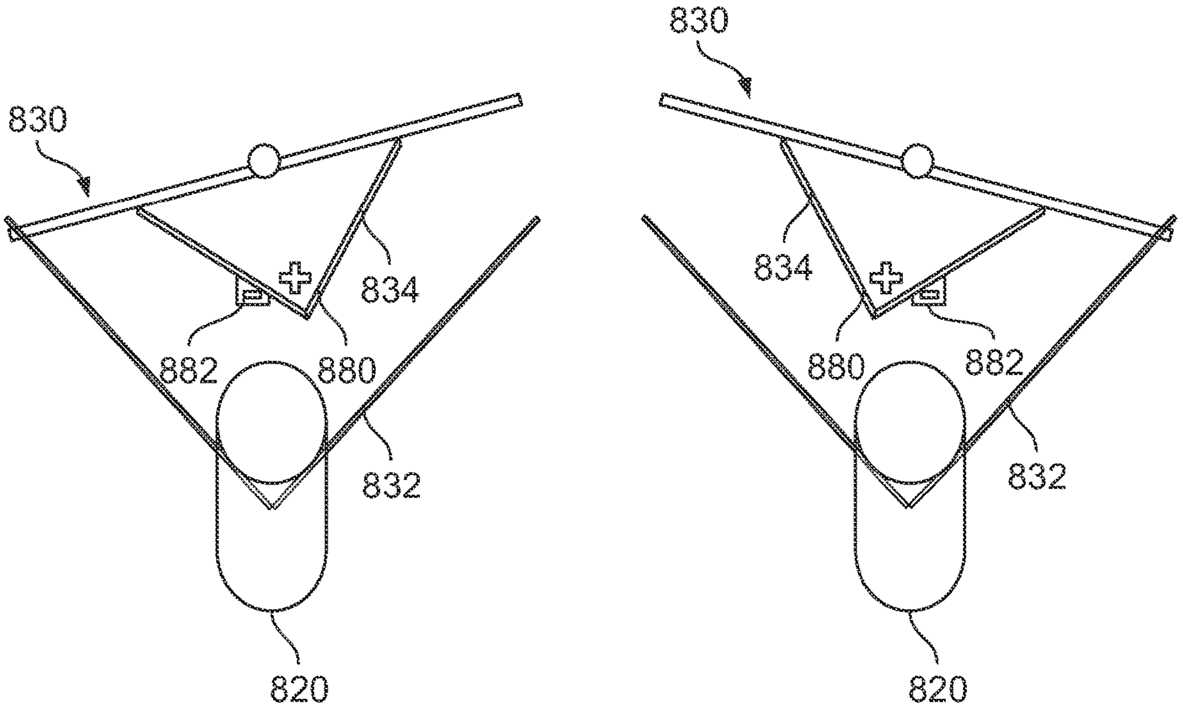
FIG. 8 illustrates an embodiment of a fluid path valve in accordance with the present disclosure.

FIG. 8 illustrates an embodiment of a fluid path valve in accordance with the present disclosure. As shown in FIG. 8, a fluid path valve 830 may include a V-feature 832 and a bistable mechanism 834. In some embodiments, bistable mechanism 834 may be associated with magnets. For example, a bottom face of path 882 and an inside wall 880 may have opposite magnetic charges. Accordingly, when detent 820 reaches the top of the path and pushes inside wall 880 over center, the opposite poles may operate to facilitate complete motion and prevent bistable mechanism 834 from passing back over center as detent 820 returns to the bottom (or corner) of V-feature 832. For example, the magnets may operate to maintain bistable mechanism 834 in contact with V-feature on a closed side of fluid path valve 830 until detent 820 engages bistable mechanism 834 to pivot bistable mechanism 834 (i.e., to prevent bistable mechanism 834 from swinging back after detent 820 moves toward the V-section (inner corner) of V-feature 832). This embodiment may be used in the system shown in earlier figures. Additionally or alternatively, there may be sufficient friction in the fluid path valve 830 such that when the bistable mechanism 834 rotates to one side, the friction in the fluid path valve 830 prevents the bistable mechanism 834 from rotating back to the center or toward the other side, until it is contacted again by detent 820.

Figure 9:
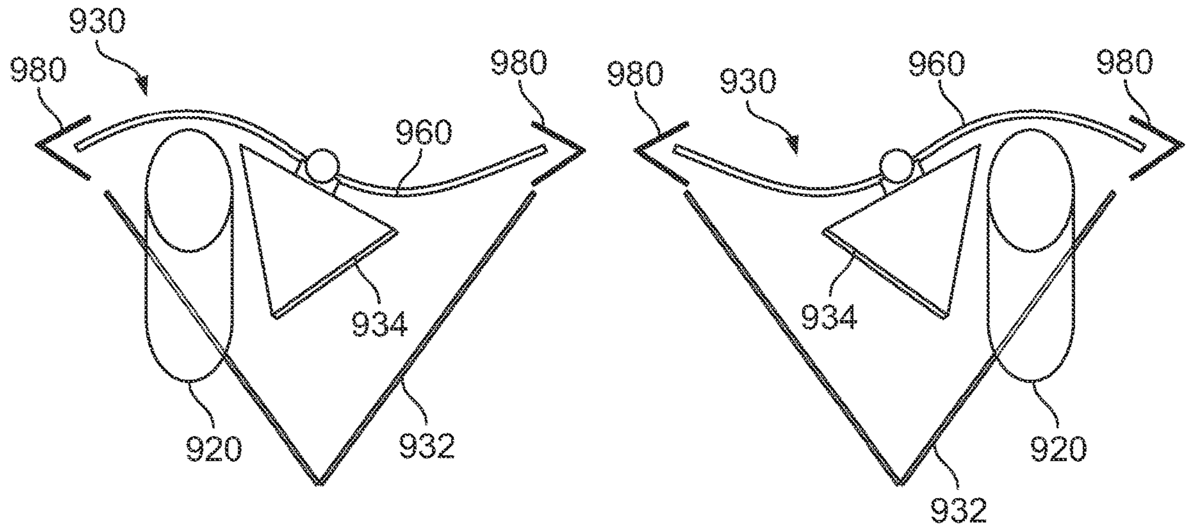
FIG. 9 illustrates an embodiment of a fluid path valve in accordance with the present disclosure.

FIG. 9 illustrates an embodiment of a fluid path valve in accordance with the present disclosure. As shown in FIG. 9, a fluid path valve 930 may include a V-feature 932 and a bistable mechanism 934. In some embodiments, a beam 960 may be fixed at the center where it is connected to the inner walls of the path, constrained on either side 980 of fluid path valve 930.

When detent 920 reaches a top of the path, detent 920 may cause the bends of beam 860 to invert, pushing the inner wall of bistable mechanism 934 over center. The bending forces and stresses of beam 960 may facilitate complete motion and prevent bistable mechanism 934 from passing back over center as detent 920 returns to the bottom (or corner) of V-feature 932. This embodiment may be used in the system shown in earlier figures.

Figure 10:
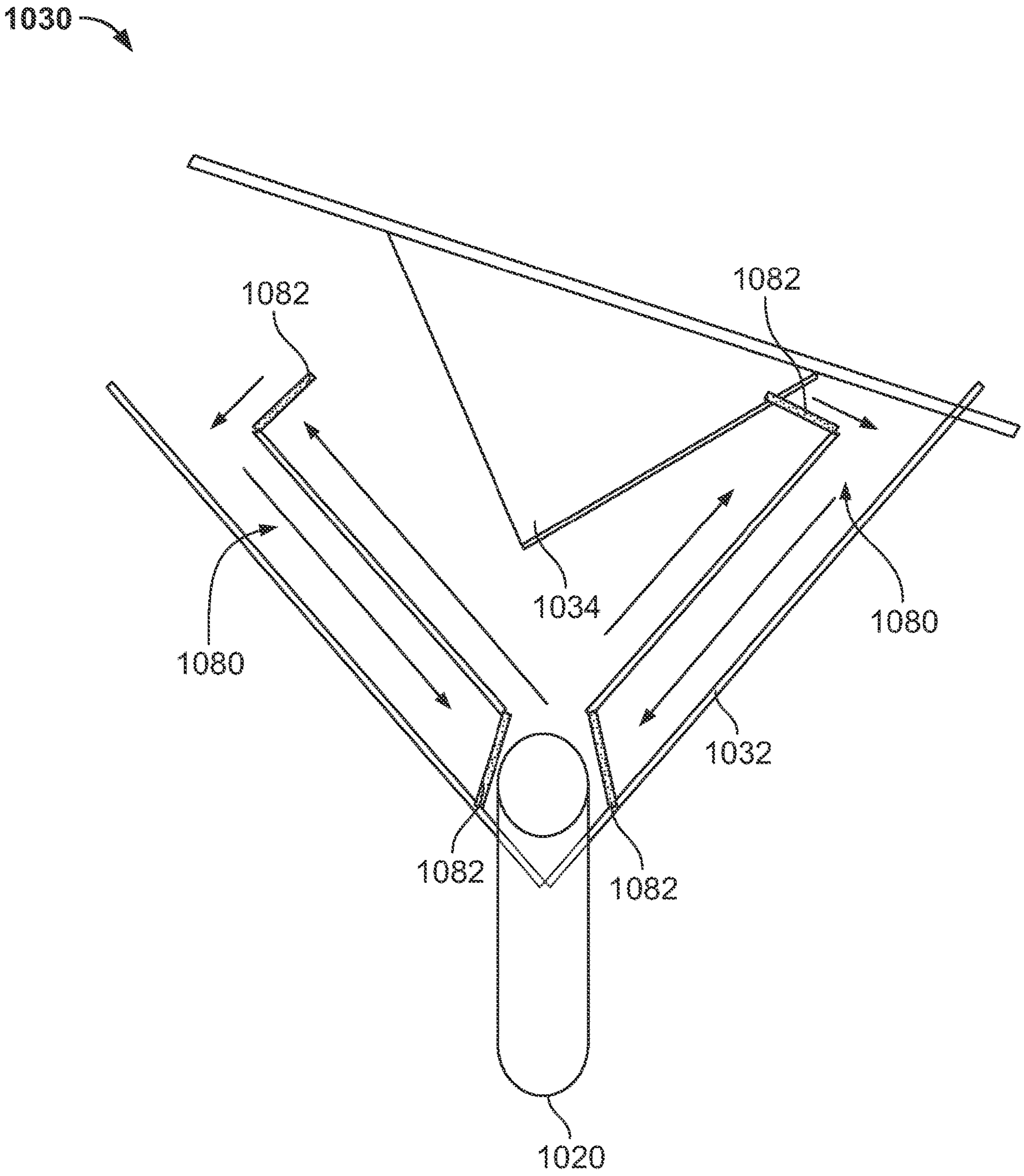
FIG. 10 illustrates an embodiment of a fluid path valve in accordance with the present disclosure.

FIG. 10 illustrates an embodiment of a fluid path valve in accordance with the present disclosure. As shown in FIG. 10, a fluid path valve 1030 may include a V-feature 1032 and a bistable mechanism 1034. V-feature 1032 may be associated with drop offs 1082 that may form paths or channels 1080. In some embodiments, drop offs 1082 may cause detent 1020 to only move in the direction indicated by the arrows (and in the opposite direction during a return process) in FIG. 10, thereby preventing detent 1020 from touching the inner wall (for instance, bistable mechanism 1034) and rotating it as detent 1020 moves toward the corner of V-feature 1032, for example, only contacting bistable mechanism 1034 when traveling toward bistable mechanism and not when traveling away from bistable mechanism 1034 toward corner of V-feature 1032. In some embodiments, the paths 1080 may slope up (for instance, out of the page of FIG. 10) in the direction of the arrows of FIG. 10. This embodiment may be used in the system shown in earlier figures.

While the present disclosure has been illustrated and described in detail in the drawings and foregoing description, the same is to be considered as illustrative and not restrictive in character, it being understood that only the certain embodiments have been shown and described and that all changes, alternatives, modifications and equivalents that come within the spirit of the disclosure are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the present disclosure, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A fluid pump system for a wearable fluid delivery device, comprising:
- a pump chamber to store a fluid;
- a fluid path in fluid communication with the pump chamber and a reservoir;
- a fluid path valve operative to control a state of the fluid path, the fluid path valve comprising a fixed portion and a movable portion; and
- a shaft configured to move along the fixed portion to directly engage the movable portion responsive to a force imparted by an actuator, the movable portion comprising an offset to deflect a force of the shaft to cause the movable portion to pivot from one of a first position or a second position to the other of the first position or the second position responsive to being engaged by the shaft to change the state of the fluid path, the offset comprising a substantially triangular projection extending from the movable portion.

2. The pump system of claim 1, the wearable fluid delivery device configured to deliver a medicament to a patient, the medicament comprising insulin.

3. The pump system of claim 1, the fixed portion comprising a V-feature having a substantially V-shape.

4. The pump system of claim 3, the V-feature comprising at least one channel for the shaft to travel during operation of the fluid path valve.

5. The pump system of claim 4, the at least one channel comprising a sloped channel with at least one drop-off element to prevent the shaft from engaging an inner wall of the movable portion when traveling toward a central V-section of the V-feature.

6. The pump system of claim 1, the movable portion comprising a bistable mechanism.

7. The pump system of claim 1, the state of the fluid path comprising one of a fluid delivery state to deliver the fluid to the patient from the pump chamber or a fluid fill state to fill the pump chamber from the reservoir.

8. The pump system of claim 1, the actuator comprising a shape memory alloy.

9. The pump system of claim 1, the shaft comprising a detent arm.

10. The pump system of claim 1, the movable portion associated with a first magnet attracted to a portion of the fixed portion to maintain the movable portion in contact with the fixed portion on a closed side of the fluid path valve until the shaft engages the movable portion to pivot the movable portion.

11. A fluid pump system for a wearable fluid delivery device, comprising:

a pump chamber to store a fluid;

a fluid path in fluid communication with the pump chamber and a reservoir;

a fluid path valve operative to control a state of the fluid path, the fluid path valve comprising a fixed portion and a movable portion;

a shaft configured to move along the fixed portion to directly engage the movable portion responsive to a force imparted by an actuator, the movable portion comprising an offset to deflect a force of the shaft to cause the movable portion to pivot from one of a first position or a second position to the other of the first position or the second position responsive to being engaged by the shaft to change the state of the fluid path; and a spring configured to bias the shaft in a direction toward the movable portion in the absence of the force of the actuator.

12. A wearable fluid delivery device, comprising:

a reservoir to store a fluid;

a needle to infuse the fluid into a patient; and a fluid pump to pump the fluid through the needle, the fluid pump comprising:

a pump chamber to store a fluid, a fluid path in fluid communication with the pump chamber and the reservoir, a fluid path valve operative to control a state of the fluid path, the fluid path valve comprising a fixed portion and a movable portion, and a shaft configured to move along the fixed portion to directly engage the movable portion responsive to a force imparted by an actuator, the movable portion comprising an offset to deflect a force of the shaft to cause the movable portion to pivot from one of a first position or a second position to the other of the first position or the second position responsive to being engaged by the shaft to change the state of the fluid path, the offset comprising a substantially triangular projection extending from the movable portion.

13. The wearable fluid delivery device of claim 12, the fixed portion comprising a V-feature having a substantially V-shape and the movable portion comprising a bistable mechanism, the V-feature comprising at least one channel for the shaft to travel during operation of the fluid path valve, and the at least one channel comprising a sloped channel with at least one drop-off element to prevent the shaft from engaging an inner wall of the movable portion when traveling toward a central V-section of the V-feature.

14. The wearable fluid delivery device of claim 12, the state of the fluid path comprising one of a fluid delivery state to deliver the fluid to the patient from the pump chamber or a fluid fill state to fill the pump chamber from the reservoir in fluid communication with the fluid path.

15. The wearable fluid delivery device of claim 12, the actuator comprising a shape memory alloy.

16. The wearable fluid delivery device of claim 12, further comprising a spring configured to bias the shaft in a direction toward the movable portion in the absence of the force of the actuator.

17. The wearable fluid delivery device of claim 12, the movable portion associated with a first magnet attracted to a portion of the fixed portion to maintain the movable portion in contact with the fixed portion on a closed side of the fluid path valve until the shaft engages the movable portion to pivot the movable portion.

18. A method of manufacturing a wearable medicament delivery device, the method comprising:

providing a reservoir configured to hold the medicament;

providing a pump system operatively coupled to the reservoir, the pump system comprising:

a pump chamber to store a fluid, a fluid path in fluid communication with the pump chamber and the reservoir, a fluid path valve operative to place a fluid path into one of a fluid fill state or a fluid delivery state, the fluid path valve comprising a fixed portion and a movable portion, and a shaft configured to move along the fixed portion to directly engage the movable portion responsive to a force imparted by an actuator, the movable portion comprising an offset to deflect a force of the shaft to cause the movable portion to pivot from one of the fluid fill state to the fluid delivery state to the other of the fluid fill state to the fluid delivery state responsive to being engaged by the shaft to change the state of the fluid path, the offset comprising a substantially triangular projection extending from the movable portion; and providing a needle configured to receive the medicament from the pump system when the fluid path valve is in the fluid delivery state for delivery to a patient.

19. A fluid pump system for a wearable fluid delivery device, comprising:

a pump chamber to store a fluid;

a fluid path in fluid communication with the pump chamber and a reservoir;

a fluid path valve operative to control a state of the fluid path, the fluid path valve comprising a fixed portion and a movable portion; and a shaft comprising a detent arm configured to move along the fixed portion responsive to a force imparted by an actuator, wherein the fixed portion comprises a V-feature having a substantially V-shape, and wherein the movable portion comprises a substantially triangular projection extending from the movable portion to deflect a force of the shaft to cause the movable portion to pivot in one step from a first position to a second position, and in another step from the second position to the first position, responsive to being engaged by the shaft to change the state of the fluid path.

* * * * *